United States Patent [19]
Rudko

[11] Patent Number: 5,125,924
[45] Date of Patent: Jun. 30, 1992

[54] HEART-SYNCHRONIZED VACUUM-ASSISTED PULSED LASER SYSTEM AND METHOD

[75] Inventor: Robert I. Rudko, Holliston, Mass.

[73] Assignee: Laser Engineering, Inc., Milford, Mass.

[21] Appl. No.: 586,884

[22] Filed: Sep. 24, 1990

[51] Int. Cl.⁵ .............................................. A61B 17/36
[52] U.S. Cl. ........................................ 606/12; 606/19;
        128/395; 372/25; 372/38; 372/58; 372/59
[58] Field of Search ...................................... 606/2-7,
        606/10-18; 128/395-398; 219/121.6-121.62;
        372/55, 58, 59, 25, 38

[56] References Cited
U.S. PATENT DOCUMENTS

| | | | |
|---|---|---|---|
| 4,512,762 | 4/1985 | Spears | 604/21 |
| 4,788,975 | 12/1988 | Shturman et al. | 606/7 |
| 4,817,111 | 3/1989 | Nilsen et al. | 372/58 |
| 4,862,886 | 9/1989 | Clarke et al. | 606/7 |
| 5,041,108 | 8/1991 | Fox et al. | 606/7 |

Primary Examiner—David M. Shay
Attorney, Agent, or Firm—Iandiorio & Dingman

[57] ABSTRACT

A heart-synchronized vacuum-assisted pulsed laser technique generates a valve control signal in response to the ECG of a beating heart which is to be synchronized with the laser; the valve control signal is applied to a valve to open it and permit laser gas to be delivered to the gas inlet of the laser assisted by the draw from a vacuum source at the gas outlet of the laser, to produce a predetermined range of laser gas pressure in the laser; the valve control signal is ceased after the predetermined range of laser gas pressure has been reached to end the gas flow through the laser and enable the rebuilding of the vacuum in the vacuum source; and a laser firing signal is generated to fire the laser when the laser gas pressure is in the predetermined range.

8 Claims, 2 Drawing Sheets

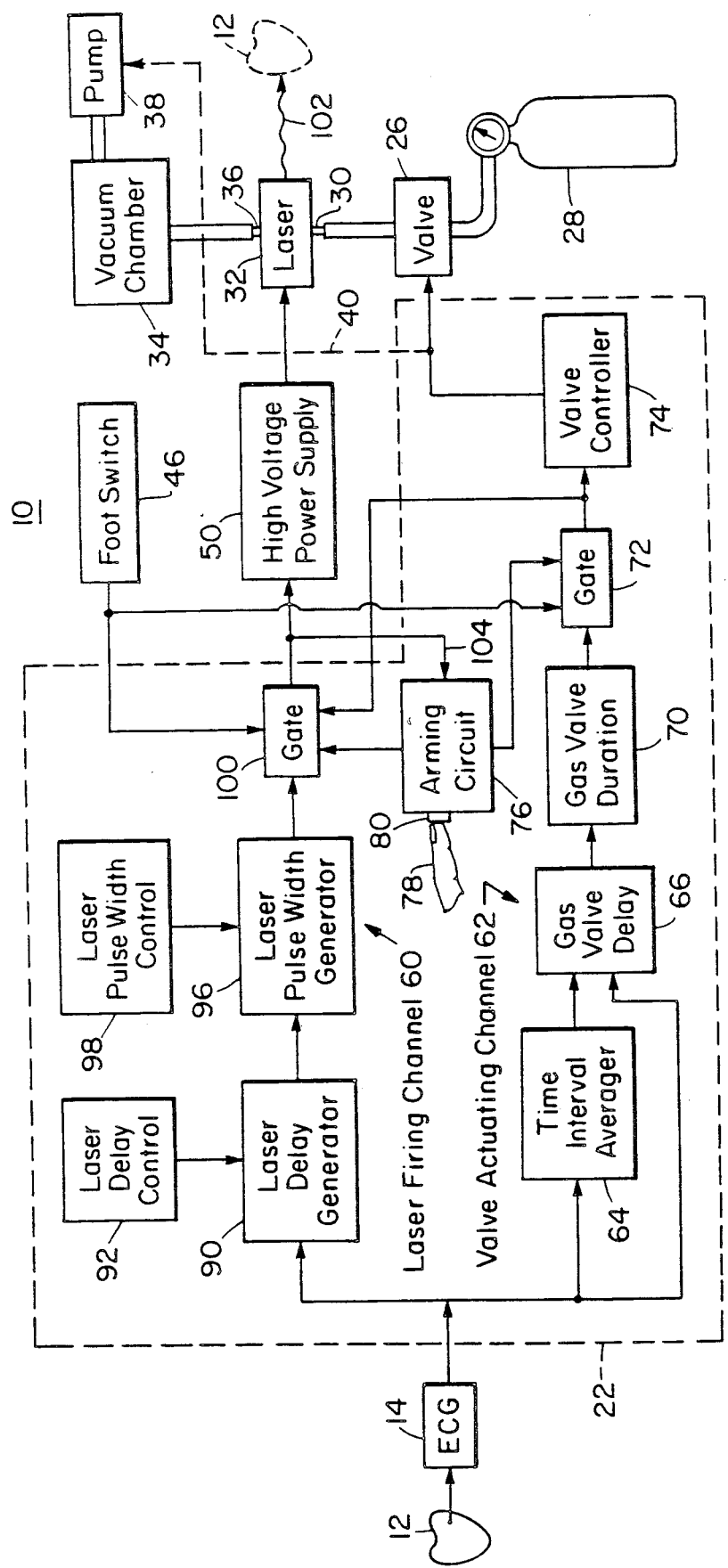

5,125,924

HEART-SYNCHRONIZED VACUUM-ASSISTED PULSED LASER SYSTEM AND METHOD

FIELD OF INVENTION

This invention relates to a heart-synchronized, vacuum assisted, pulsed laser system and method, and more particularly to such a system and method which operates on a beating heart between the R and T waves using a vacuum assist to create intermittent fast flow laser gas conditions for creating long laser pulses.

RELATED CASES

This application is related to and incorporates herein by reference the following applications having common inventors and assignee and filed on even date herewith:

"Heart-Synchronized Pulsed Laser System", by Robert I. Rudko and Stephen J. Linhares U.S. application Ser. No. 586,951;

"Long Pulse, Fast Flow Laser System and Method", by Robert I. Rudko U.S. application Ser. No. 586,885, now U.S. Pat. No. 5,109,388 and "Handpiece for Transmyocardial Vascularization Heart-Synchronized Pulsed Laser System", by Robert I. Rudko (Docket No. LE-111J).

BACKGROUND OF INVENTION

Laser implemented transmyocardial revascularization shows great promise for heart patients, but it does have some medical obstacles associated with it. The heart is extremely sensitive to laser pulses at certain times during its cycle. A laser pulse striking the heart at the T time of the ECG wave, for example, could cause the heart to fibrillate and result in heart failure. If the heart is stopped during the procedure this problem can be avoided. But stopping the heart requires cooling the heart and connecting the patient to a heart-lung machine with all the attendant increased risks that this brings including prolonged recovery times. A beating heart, on the other hand, is difficult to administer this technique to because as the heart contracts and expands the surface may not remain normal to the laser beam, the heart wall changes distance from the focus of the beam, and the thickness of the wall changes so that the positioning of the laser handpiece and the power of the beam required are varying and unpredictable. This makes precise location of laser beam on the heart difficult so that not only will the holes not be properly located, but other areas of the heart which should not be struck may well be struck.

Laser implemented transmyocardial revascularization also raises problems of a technical nature: lasers suitable for generating pulses of the necessary power and duration are quite expensive. One approach to creating such pulses in a continuous laser is to maintain a continuous electrical discharge in the laser but flow the gas through the discharge region at such a velocity that the gas is only in the discharge region for a short time. While each volume of gas responds as if pulsed, the effect is in fact a continuous laser with ten times the power of slow flow or of a sealed laser.

However, to obtain such high-speed gas flow a high-speed gas pump and a heat exchanger capable of cooling the gas are required. These are expensive, large, noisy, and consume substantial power. But this is a preferred approach in many medium and low-speed pulsed laser systems.

In some applications, pulses of longer duration are required which are too long to obtain the energy conversion without heating the gas and thus decreasing the population inversion ratio yet are not long enough to require continuous high speed gas flow. Thus it is inefficient and expensive to maintain the high-speed pump and heat exchanger continuously for these applications.

SUMMARY OF INVENTION

It is therefore an object of this invention to provide an improved heart-synchronized, vacuum assisted, pulsed laser system and method.

It is a further object of this invention to provide such an improved heart-synchronized, vacuum assisted, pulsed laser system and method for use in transmyocardial revascularization.

It is a further object of this invention to provide such an an improved heart-synchronized, vacuum assisted, pulsed laser system and method which is synchronized to operate at a specific time in the heart beating cycle when accuracy is enhanced and risks are reduced.

It is a further object of this invention to provide an improved heart-synchronized, vacuum assisted, long pulse, fast flow laser system and method with substantially increased power at reduced cost.

It is a further object of this invention to provide such an improved heart-synchronized, vacuum assisted, long pulse, fast flow laser system and method which is simpler, uses fewer components and is easier and less expensive to build and maintain and is smaller, more compact and lower in weight.

It is a further object of this invention to provide such an improved heart-synchronized, vacuum assisted, long pulse, fast flow laser system and method which achieves high-power laser output of an electrically pulsed or fast flow continuous laser without the attendant cost and complexity typically associated with such units.

The invention results from the realization that a long pulse, low duty cycle laser can be constructed having the increased power output of a fast flow pulsed laser without the need for expensive pumps and heat exchangers by providing the fast flow only intermittently in conjunction with the pulse period using a vacuum storage technique which builds up a vacuum during the off-time and applies that vacuum to drive the gas flow through the laser at high speed during the pulse time; and that such a long pulse, low duty cycle laser beam can be synchronized for operating on a beating heart accurately, with minimal interference with the heart and minimal risk to the patient by synchronizing the pulsing of the laser to the ECG of the heart so that laser pulses can be administered to the heart only during the moment when the heart is most still, least sensitive electrically, during the period from the R to the T wave of the ECG. It should be understood that throughout the specification and claims the term "vacuum" is used as a shorthand expression to refer simply to the negative pressure condition and not necessarily a perfect or nearly perfect vacuum: significant negative pressure is sufficient.

This invention features a heart-synchronized vacuum assisted pulsed laser system. There is a laser having a laser beam delivery system, a gas inlet, a gas outlet, and electrical discharge electrodes. Valve means interconnect the gas inlet to a source of laser gas. Vacuum storage means are connected to the laser gas outlet. There are means responsive to the ECG signal of the beating heart to be synchronized with the laser, for generating a valve control signal for opening the valve and enabling the laser gas to be drawn from the source of laser gas through the laser and into the vacuum storage means to produce a predetermined range of laser gas pressure in the laser. The valve control signal closes the valve means after the predetermined range of laser gas pressure is reached, to end the gas flow through the laser and enable rebuilding of the vacuum in the vacuum storage means. There are further means responsive to the ECG signal of the beating heart to be synchronized with the laser, for generating a laser firing signal when the laser gas pressure is in the predetermined range, for firing the laser to strike the beating heart.

In a preferred embodiment, the vacuum storage means includes a vacuum chamber and a pump for evacuating the chamber. The means for generating a valve control signal may include means for determining the average period of the ECG heart cycle. The means for generating a valve control signal may further include means responsive to the means for determining the average period of the ECG heart cycle and to the ECG, for initiating the valve control signal between R waves of the ECG and setting the duration of the valve control signal to produce the predetermined range of laser gas pressure in the laser during the occurrence of the R wave of the ECG heart cycle. The means for generating a valve control signal may further include valve gate means for inhibiting delivery of the valve control signal to the valve means, and switch means for selectively enabling the valve gate means to pass the valve control signal through the valve gate means.

The means for generating a laser firing signal may include means for initiating the laser firing signal between R waves of the ECG and setting the duration of the laser firing signal to fire the laser proximate the R wave of the ECG when the laser gas pressure is in the predetermined range. The means for generating a laser firing signal may further include laser gate means for inhibiting delivery of the laser firing signal to the laser and switch means for selectively enabling the laser gate means to pass the laser firing signal to the laser.

The invention also features a heart-synchronized vacuum assisted pulsed laser method, which includes generating a valve control signal in response to the ECG of a beating heart to be synchronized with the laser, and applying the control signal to a valve to open the valve to permit laser gas from a source of laser gas to be delivered to the gas inlet of the laser, assisted by the draw of a vacuum source at the gas outlet of the laser to produce a predetermined range of laser gas pressure in the laser. The valve control signal is ceased after the predetermined range of laser gas pressure has been reached to end the gas flow through the laser and enable the rebuilding of the vacuum in the vacuum source. A laser firing signal is generated for firing the laser when the laser gas pressure is in the predetermined range.

DISCLOSURE OF PREFERRED EMBODIMENT

Other objects, features and advantages will occur to those skilled in the art from the following description of a preferred embodiment and the accompanying drawings, in which:

FIG. 3 is a more detailed schematic diagram of the controller of FIG. 1.

Figure 1:
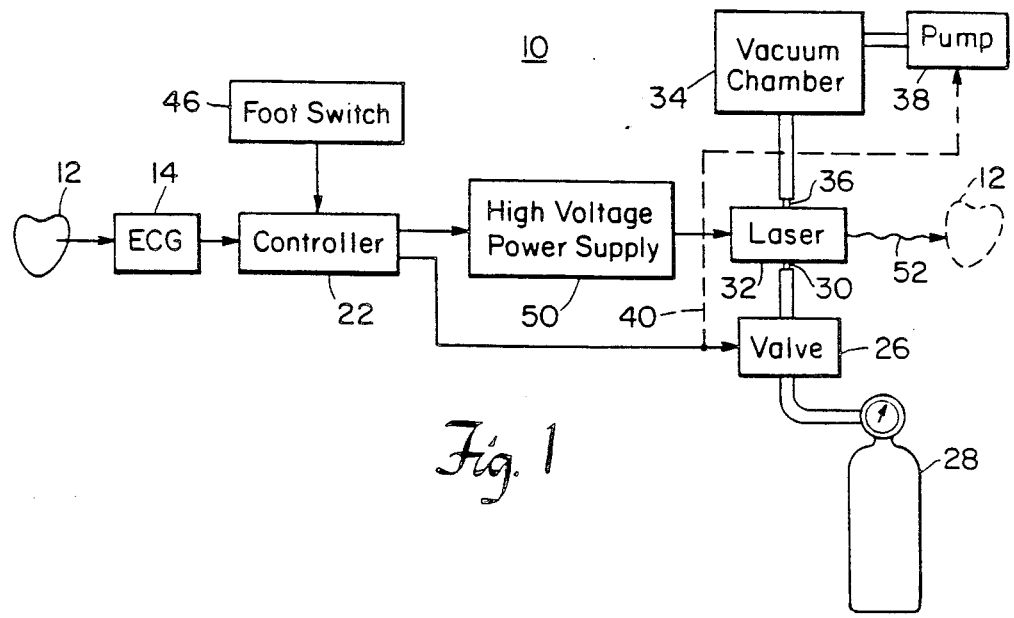
FIG. 1 is a simplified block diagram of a heart-synchronized vacuum assisted pulsed laser system according to this invention.
Figure 2:
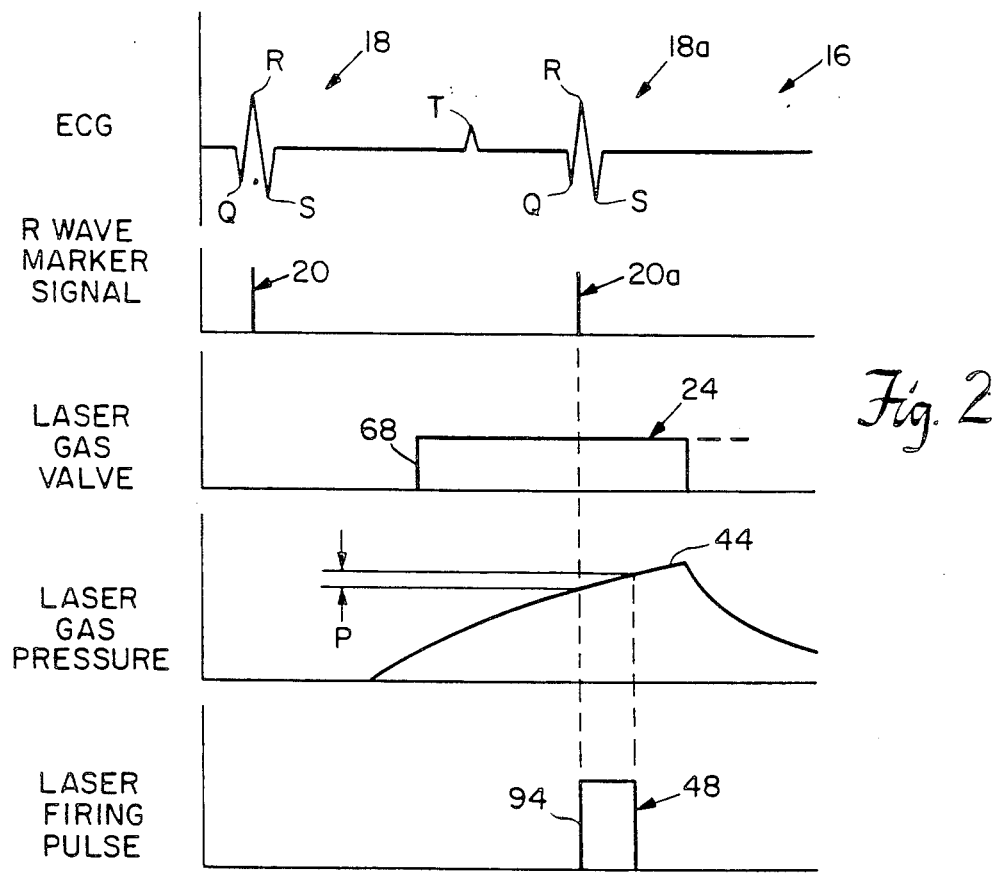
FIG. 2 is an illustration of wave forms occurring at various points in the system of FIG. 1.

There is shown in FIG. 1 a heart-synchronized vacuum pulsed laser system 10 according to this invention. The patient whose beating heart is to be operated on is connected to an electrocardiogram unit 14 which provides the electrocardiogram 16, FIG. 2, that includes recurring heart cycles 18, 18a including Q, R, S and T waves. This electrocardiogram signal, or preferably simply the R wave marker signal 20, FIG. 2, is delivered to controller 22, FIG. 1. The controller constantly determines the average period of the heart wave cycles 18, 18a, or preferably the period between R wave marker signals 20, 20a. From this controller 22 determines the proper time to trigger the laser gas valve signal 24, FIG. 2, which operates valve 26, FIG. 1. A suitable ECG unit is a Model HP 78352A made by Hewlett-Packard Company. When valve 26 is actuated it permits the laser gas, which is a mixture of helium, carbon dioxide and nitrogen, typically under a pressure of 60 psi, to be delivered from laser gas source 28 to laser gas inlet 30 of $CO_2$ laser 32. Pressurized laser gas flows through laser 32 assisted by the draw of the vacuum in vacuum chamber 34 which is connected to laser gas outlet 36. The vacuum chamber 34 is maintained by a pump 38. The duration of the operation of valve 26 is so short that pump 38 may be set to simply respond to a decrease in the vacuum in vacuum chamber 34 to energize and attempt to reestablish the vacuum. Or, when the actuating signal to valve 26 is ceased, that change in condition may be reflected over line 40 to pump 38 to command it to begin pumping only after the valve 26 has once again closed. In either case, the laser gas valve 24, FIG. 2, is timed so that the laser gas pressure reaches a pressure range, P, as indicated by the laser gas pressure wave 44, FIG. 2, such as 50 to 150 torr, during the occurrence of the R wave or R wave marker signal 20. At this point, provided the surgeon has operated foot switch 46, a laser firing pulse 48, FIG. 2, is generated by controller 22 and directed to high-voltage power supply 50, which fires lasers 32 during the period when the laser gas pressure is in the range P and produces a laser beam 52 which strikes beating heart 12 at precisely the right moment proximate the occurrence of the R wave.

Controller 22 includes a laser firing channel 60 and a valve actuating channel 62. Valve actuating channel 62 includes a time interval averager circuit 64, which determines the average time from R wave to R wave in the heart cycles of the ECG. This signal, together with the R wave marker signal itself, is delivered to gas valve delay circuit 66. It is this circuit which determines the start time for the leading edge 68 of laser gas valve signal 24, FIG. 2, which is empirically determined to provide sufficient time for the laser gas pressure wave 44 to reach the proper range P of pressure at the time the R wave occurs. The duration of the laser gas valve signal 24 is determined by gas valve duration circuit 70, which keeps valve 26 open long enough to gain the desired pressure range P, and then shuts off valve 26 after the laser has been fired to enable the vacuum in chamber 34 to be reconstituted by pump 38. Each time a marker pulse is sensed, valve actuating channel 62 provides the laser gas valve signal 24 to gate 72. However, gate 72 only passes that signal to valve controller circuit 74, which then operates valve 26, if gate 72 has received two signals: one from the actuation of foot switch 46 by the surgeon, the other from arming circuit 76, which may be operated for example by simply pressing a finger 78 against an actuator button 80. The arming circuit ensures that accidental operation of the foot switch will not cause the system to fire a laser beam at the heart.

At the same time that the ECG signals or R wave marker signals are being delivered to channel 62, they are also being delivered to laser firing channel 60. There, laser delay generator circuit 90, under control of laser delay control circuit 92, sets the position of the leading edge 94, FIG. 2, of the laser firing pulse 48 so that it occurs coincident with or approximately coincident with the R wave or R wave marker signal 20. The width of laser firing pulse 48 is set by laser pulse width generator circuit 96 under control of the laser pulse width control circuit 98. The width is set to provide sufficient energy in the laser beam to puncture the wall of the heart undergoing the surgery. Laser pulse 48, like laser gas valve signal 24, is generated at each heart cycle upon the occurrence of the R wave or the R wave marker signal. However, it will not be passed by gate 100 unless that gate is enabled. Gate 100 is enabled by the coincidence of three signals: one from foot switch 46, one from arming circuit 76, and a third from the output of gate 72 indicating that the valve 26 has been opened and gas flow has been established through laser 32. When all of these events occur, gate 100 is enabled to pass laser firing pulse 48 to high-voltage power supply 50, which then in turn fires laser 32 and produces the beam 102 which strikes heart 12. As soon as the laser firing pulse 48 is passed by gate 100, a signal is delivered on line 104 to disable arming circuit 76 so that the system cannot be fired again by merely holding down the foot switch: the arming circuit must be newly actuated before foot switch 46 is again functional.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A heart-synchronized, vacuum assisted, pulsed laser system comprising:
 - a laser having a laser beam delivery system and including a gas inlet, a gas outlet and electrical discharge electrodes;
 valve means for selectively opening and closing said gas inlet to a source of laser gas;
 vacuum storage means connected to said gas outlet; and
 controller means for synchronizing an ECG signal with said laser including
  means to receive an ECG signal of a beating heart,
  valve control means, responsive to the ECG signal, for generating a valve control signal having a duration,
  for opening said valve means enabling the laser gas to be drawn from the source of laser gas into said laser assisted by said vacuum storage means for a predetermined time period to produce a predetermined range of laser gas pressure in said laser, and
  for closing said valve means after said predetermined range of laser gas pressure has been reached to end the gas flow through said laser and enable regeneration of the vacuum in said vacuum storage means, and
 laser firing signal means, responsive to the ECG signal, for generating a laser firing signal when said laser gas pressure is in said predetermined range which enables said laser to fire a laser beam to strike the beating heart.

2. The heart-synchronized, vacuum assisted, pulsed laser system of claim 1 in which said vacuum storage means includes a vacuum chamber and a pump means for evacuating said chamber.

3. The heart-synchronized, vacuum assisted, pulsed laser system of claim 1 in which said valve control means further includes valve gate means for inhibiting delivery of said valve control signal to said valve means, and switch means for selectively enabling said valve gate means to pass said valve control signal to said valve means.

4. The heart-synchronized, vacuum assisted pulsed laser system of claim 1 in which said laser firing signal means includes means for initiating said laser firing signal between R waves of the ECG signal and setting the duration of said laser firing signal to fire said laser proximate the R wave of the ECG when the laser gas pressure is in said predetermined range.

5. The heart-synchronized, vacuum assisted, pulsed laser system of claim 1 in which said laser firing signal means further includes laser gate means for inhibiting delivery of said laser firing signal to said laser, and switch means for selectively enabling said laser gate means to pass said laser firing signal to said laser.

6. The heart-synchronized, vacuum assisted, pulsed laser system of claim 1 in which said valve control means includes means for determining an average period of the ECG heart cycle.

7. The heart-synchronized, vacuum assisted, pulsed laser system of claim 6 in which said valve control means further includes means, responsive to said means for determining the average period of the ECG heart cycle and to the ECG signal, for initiating said valve control signal between R waves of the ECG signal and setting the duration of said valve control signal to produce said predetermined range of laser gas pressure in the laser during the occurrence of the R wave of the ECG heart cycle.

8. A heart-synchronized, vacuum assisted, pulsed laser transmyocardial vascularization method comprising:
 generating a valve control signal, in response to an ECG signal of a beating heart, for synchronizing said ECG signal with a laser;
 applying the valve control signal to a valve to open the valve and permit laser gas from a source of laser gas to be delivered to a gas inlet of the laser assisted by the draw from a vacuum source at a gas outlet of the laser to produce a predetermined range of laser gas pressure in the laser;
 ceasing the valve control signal after the predetermined range of laser gas pressure has been reached to end the gas flow through the laser and enable the rebuilding of the vacuum in the vacuum source; and
 generating a laser firing signal for firing the laser when the laser gas pressure is in the predetermined range.

* * * * *